(12) United States Patent
Ferri

(10) Patent No.: US 9,199,960 B2
(45) Date of Patent: Dec. 1, 2015

(54) METHOD AND APPARATUS FOR PROCESSING HERBACEOUS PLANT MATERIALS INCLUDING THE CANNABIS PLANT

(71) Applicant: Frederick R. Ferri, North Scituate, RI (US)

(72) Inventor: Frederick R. Ferri, North Scituate, RI (US)

( * ) Notice: Subject to any disclaimer, the term of this patent is extended or adjusted under 35 U.S.C. 154(b) by 0 days.

(21) Appl. No.: 14/182,631

(22) Filed: Feb. 18, 2014

(65) Prior Publication Data

US 2014/0330030 A1 Nov. 6, 2014

Related U.S. Application Data

(60) Provisional application No. 61/818,649, filed on May 2, 2013.

(51) Int. Cl.
*A61K 36/185* (2006.01)
*C07D 311/92* (2006.01)
*C07C 37/00* (2006.01)

(52) U.S. Cl.
CPC ............ *C07D 311/92* (2013.01); *A61K 36/185* (2013.01); *C07C 37/004* (2013.01); *A61K 2236/00* (2013.01)

(58) Field of Classification Search
USPC .................................. 424/725, 774
IPC .................................... A61K 36/185
See application file for complete search history.

(56) References Cited

U.S. PATENT DOCUMENTS

| | | | |
|---|---|---|---|
| 3,735,964 A | 5/1973 | Lorenzen | |
| 4,279,824 A | 7/1981 | McKinney | |
| 4,528,289 A | 7/1985 | Jaggy et al. | |
| 8,337,908 B2 | 12/2012 | Letzel et al. | |
| 2003/0017216 A1 | 1/2003 | Schmidt et al. | |
| 2004/0033280 A1* | 2/2004 | Whittle | 424/774 |
| 2004/0034108 A1* | 2/2004 | Whittle | 514/772 |
| 2005/0049298 A1* | 3/2005 | Goodwin et al. | 514/453 |
| 2005/0165088 A1* | 7/2005 | Whittle et al. | 514/454 |
| 2005/0266108 A1* | 12/2005 | Flockhart et al. | 424/774 |
| 2006/0167283 A1 | 7/2006 | Flockhart et al. | |
| 2007/0032544 A1* | 2/2007 | Korthout et al. | 514/454 |
| 2008/0167483 A1 | 7/2008 | Whittle et al. | |
| 2010/0119606 A1* | 5/2010 | Whittle et al. | 424/484 |
| 2010/0168448 A1* | 7/2010 | Flockhart et al. | 549/390 |
| 2010/0216872 A1* | 8/2010 | Letzel et al. | 514/454 |
| 2012/0043242 A1* | 2/2012 | Hospodor | 206/438 |
| 2012/0046352 A1 | 2/2012 | Hospodor | |
| 2012/0059062 A1* | 3/2012 | Whittle et al. | 514/568 |
| 2012/0095088 A1* | 4/2012 | Hospodor | 514/454 |
| 2014/0287068 A1* | 9/2014 | Lewis et al. | 424/725 |

FOREIGN PATENT DOCUMENTS

WO 02/064109 8/2002

OTHER PUBLICATIONS

Relentless (A forum for International Cannagraphic Magazine) [bulletin board online]. Jul. 7, 2011 [retrieved on Aug. 1, 2014]. Retrieved from the internet: <URL:https://www.icmag.com/ic/shothread.php?t=216598; p. 1, lines 2-6.
How to Make Hash Oil the Easy Way. Schaffer Library of Drug Policy. [online] Mar. 2, 2013. [retrieved on Aug. 2, 2014]. Retrieved from the internet: <URL:https://web.archive.org/web/20130302162308/http:druglibrary.org/MedicalMj/hash/hashmethod1.htm; p. 1, line 2, 17, 19, 22, 24, 27.
The Oracle (A forum for Grasscity.com) [bulletin board online]. Mar. 29, 2011 [retrieved on Aug. 2, 2014]. Retrieved from the internet: <URL:http//forum.grasscity.com/incredible-edible-herb/780718-theoracles-oven-decarboxylation-technique-sativex-patent-derived-data.html; p. 1, lines 1, 28 table 4; p. 2, lines 4, 9.
New Brunswick biological shakers. Product description. [online] Eppendorf, Inc., Jan. 26, 2013. [retrieved on Aug. 2, 2014]. Retrieved from the internet: <URL: https://web.archive.org/web/20130126130018/http:/newbrunswick.eppendorf.com/en/products/shakers/; col. 1, lines 1-10; p. 1, line 1.

* cited by examiner

*Primary Examiner* — Chris R Tate
(74) *Attorney, Agent, or Firm* — Salter & Michaelson

(57) ABSTRACT

A method and associated system of treating a plant material consisting essentially of the plant *cannabis* in order to extract cannabinoids in liquid form from the plant material. The method includes heating the plant material; drying the plant material; grinding the dried plant material into a powder form; marinating the dried plant powder in a solvent for a predetermined time period to form a marinated mixture; shaking and heating the marinated mixture; filtering the mixture so that only a liquid part of the mixture remains; and evaporating from the liquid the solvent in order to provide the cannabinoid liquid extract.

16 Claims, 1 Drawing Sheet

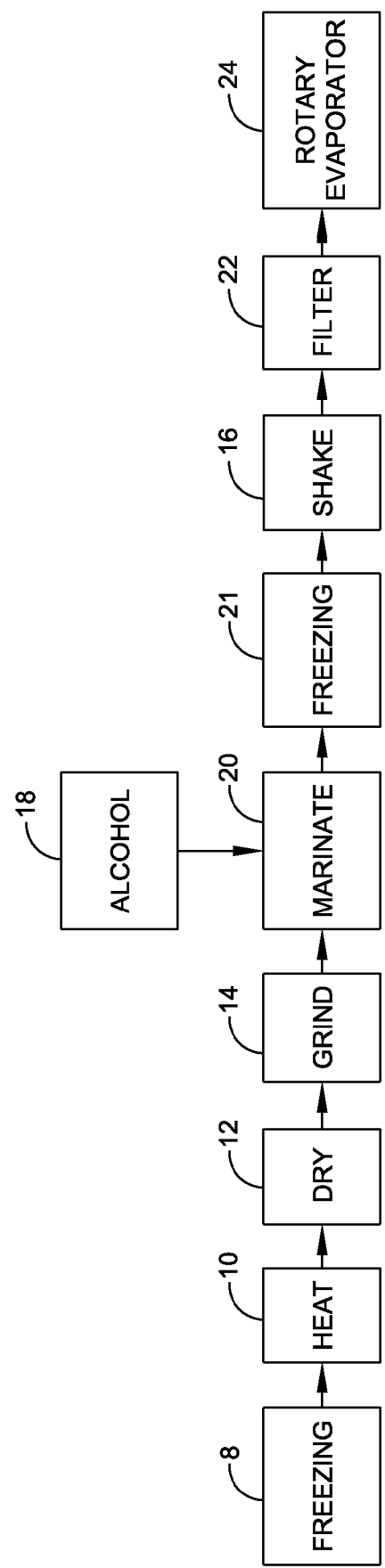

METHOD AND APPARATUS FOR PROCESSING HERBACEOUS PLANT MATERIALS INCLUDING THE CANNABIS PLANT

RELATED INFO

Priority for this application is hereby claimed under 35 U.S.C. §119(e) to commonly owned and U.S. Provisional Patent Application No. 61/818,649 which was filed on May 2, 2013 and which is incorporated by reference herein in its entirety.

FIELD OF THE INVENTION

The present invention relates to a method and apparatus for processing herbaceous plant material. More particularly, the present invention relates to a method and apparatus for processing herbaceous plant material particularly including the *cannabis* plant.

BACKGROUND OF THE INVENTION

It is known that *Cannabis* has been used for several years for medicinal purposes. Three of the main components include Delta9-Tetrahydrocannabinol (THC); Cannabinol (CBN); and Cannabidiol (CBD). A main objective of the present invention is to increase the yield of these ingredients and in particular CBD. A further objective of the present invention is to provide a *cannabis*-supported substance in liquid form.

SUMMARY OF THE INVENTION

To accomplish the foregoing and other objects, features and advantages of the present invention, in accordance with one aspect thereof, there is provided a method of treating a plant material consisting essentially of the plant *cannabis* in order to extract cannabinoids in liquid form from the plant material. The method comprises the steps of:
  heating the plant material to cause decarboxylation;
  drying the plant material;
  grinding the dried plant material into a powder form;
  providing an alcohol solvent;
  marinating the dried plant powder in the solvent for a predetermined time period to form a marinated mixture;
  shaking and heating the marinated mixture;
  filtering the mixture so that only a liquid part of the mixture remains; and
  evaporating from the liquid the solvent in order to provide the cannabinoid extract.

In accordance with other aspects of the present invention the method also includes, prior to the heating step, harvesting the plant material; includes, prior to the heating step, freezing the plant material; includes freezing the plant material for up to 24 hours; the freezing step is at a temperature range of 15-30 degrees F.; the heating step is for 20-30 minutes; the heating step is in a temperature range of 120 to 500 degrees F. or more particularly in a temperature range of 180 to 200 degrees F.; the solvent is 190 to 200 proof ethyl alcohol; the solvent is 99% isopropyl hexane; the marinating step occurs for at least 24 hours; the marinating step occurs at room temperature; including, prior to the heating step, freezing the plant material, and subsequently freezing the marinated mixture; the subsequent freezing is for at least 12 hours; the step of shaking and heating the marinated mixture occurs for at least 12 hours; the step of shaking and heating the marinated mixture is accomplished by means of placing the marinated mixture in a container placed on a heated shaker; and the step of evaporating includes evaporating by means of a rotary evaporator.

In accordance with another aspect of the present invention there is provided a system for treating a plant material consisting essentially of the plant *cannabis* in order to extract cannabinoids in liquid form from the plant material. The system comprises:
  a heater for heating the plant material to cause decarboxylation;
  a drying device for drying the plant material;
  a grinder device for grinding the dried plant material into a powder form;
  a marinator for marinating the dried plant powder in a solvent for a predetermined time period to form a marinated mixture;
  a heated shaker for shaking and heating the marinated mixture;
  a filter for filtering the mixture so that only a liquid part of the mixture remains; and
  an evaporator for evaporating from the liquid the solvent in order to provide the cannabinoid extract.

BRIEF DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings in which the sole drawing is a block diagram illustrating the method of the present invention.

DETAILED DESCRIPTION

The present invention relates to a method and associated apparatus for treating a plant material, particularly the *Cannabis* plant. For a description of the method refer to the attached block diagram, which illustrates by individual blocks the successive steps that are employed in accordance with the present invention. This includes the freezing step 8; the heating step 10; the drying step 12; the grinding step 14; and the shaking step 16. The block 20 in the diagram illustrates the marinating step 20 which combines the ground powder from step 14 with the solvent from step 18. After this marination step, is included a filtering step at 22 and an evaporation step 24 for removing any traces of alcohol.

Initially, of course, the plant material is harvested which usually includes a step of trimming the plant material. After the harvesting step, the plant material is placed in a freezer. This is shown by the freezing step 8 in the diagram. The plant material is preferably placed in the freezer for 24 hours. The freezer temperature is preferably in a range 15-30° F. After this freezing step the material is removed from the freezer to begin a heating process.

The initial step of heating is for the purpose of decarboxylation, which is a chemical reaction that removes the carboxyl group. In order to have this decarboxylation, heating is used. The heating step can be performed in any number of ways on the *Cannabis* plant material. The heating is preferably in a temperature range of 120-500° F. or more preferably a temperature range of 180-210° F. This heating step may occur in an oven that is of commercial type and that is considered conventional. After the heating step, the plant material is dried as indicated by block 12 in the block diagram.

After completing these initial steps, the material may be brought to room temperature. As illustrated in the diagram, the next step is a grinding step illustrated by box 14. This step transforms the plant material into a powder form. This grinding may be provided with any number of different pieces of apparatus. For example, a food processor, coffee bean grinder, or spice grinder may be used for grinding the material into a powder form.

The block diagram also illustrates the marinate step 20, in which the powder product is marinated by the alcohol. The alcohol may be denatured pure 200 proof ethanol alcohol of food grade, or other grades of alcohol may be used. One example of the solvent 18 is 190-200 proof ethyl alcohol, 99 percent isopropyl hexane. This marination step preferably occurs for several hours and more preferably for at least 24 hours. This marination step may occur at room temperature.

In one example of the step of marinating, in a 1,000 ml beaker add 31 grams of ground plant matter into 300 ml of solvent. Alternatively, for a 250 ml beaker, add 13 grams of ground plant matter into 100 ml of solvent.

After the marinating step, as indicated in the block diagram, there is a further freezing step 21. This freezing step may also occur in a conventional freezer at a temperature in a range of 15-30° F. This freezes both the plant material and the solvent. The freezing occurs preferably for at least 12 hours.

The block diagram also illustrates the heating and shaking step 16. The heated shaker that is used may be a conventional piece of equipment. For example, a heated shaker sold by Heidolph Instruments may be employed. For the purpose of providing this step, the material may be placed in a beaker for 12 hours on a heated shaker. The heating and shaking step is important in removing the significant properties of the plant material.

The next step illustrated by box 22 is a filtering step. The filter may be conventional filter, such as a 200 milliliter lab-grade filter. Lastly, as illustrated in the block diagram, a rotary evaporator 24 is used to essentially extract the alcohol from the *cannabis*. The extraction time for 300 ml of filtered material is approximately 20 minutes. This yields 7.5 to 8 ml of the final medicine. The process of the present invention provides a high concentration of THC, CBD, CBN, and Terpenes. The rotary evaporator 24 may be of conventional design, such as one sold by Heidolph Instruments. The rotary evaporator is a device for the efficient removal of solvents, and in this case, the alcohol. Alternatively, a Buchi Rotary Evaporator R-200 may be used. Typical components that comprise a rotary evaporator are a motor unit, a vapor duct, a vacuum system, a heated fluid bath, and a condenser.

As indicated in the block diagram, after the heating and shaking and before the rotary evaporator step, there is the important step of filtering indicated by box 22 in the block diagram. The filtering essentially removes any residual plant material leaving only the liquid introduced into the rotary evaporator. The finished product is then bottled and ready for use.

Having now described a limited number of embodiments of the present invention, it should now be apparent to those skilled in the art that numerous other embodiments and modifications thereof are contemplated as falling within the scope of the present invention, as defined by the appended claim.

What is claimed is:

1. A method of treating a *Cannabis* plant material to obtain a cannabinoid-enriched extract, said method comprising the steps of:
    initially freezing the plant material;
    heating the initially frozen plant material to cause decarboxylation of the cannabinoids therein;
    drying the heated plant material;
    grinding the dried plant material into a powder form;
    soaking the dried plant material in a solvent for a predetermined time period to form a soaked mixture;
    subsequently freezing the soaked mixture;
    shaking and heating the subsequently frozen soaked mixture by means of a heated shaker;
    filtering the shaken and heated mixture so that only a liquid portion of the mixture remains;
    evaporating the solvent from the liquid portion to obtain said cannabinoid-enriched extract.

2. The method of claim 1 further comprising, prior to the heating step, harvesting the plant material.

3. The method of claim 1 wherein the initial freezing step comprises freezing the plant material for up to 24 hours at a temperature range of 15-30° F., and the subsequent freezing step comprises freezing the soaked mixture for up to 12 hours at a temperature range of 15-30° F.

4. The method of claim 1 wherein the initial freezing step comprises freezing the plant material for up to 24 hours.

5. The method of claim 1 wherein the initial and subsequent freezing steps is at a temperature range of 15-30° F.

6. The method of claim 1 wherein the heating step is for 20-30 minutes.

7. The method of claim 1 wherein the heating step is in a temperature range of 120 to 500° F.

8. The method of claim 1 wherein the heating step is in a temperature range of 180 to 200° F.

9. The method of claim 1 wherein the solvent is 190 to 200 proof ethyl alcohol.

10. The method of claim 1 wherein the solvent is a mixture of isopropyl alcohol and hexane.

11. The method of claim 1 wherein the soaking step occurs for at least 24 hours.

12. The method of claim 1 wherein the soaking step occurs at room temperature.

13. The method of claim 1 wherein the subsequent freezing step is for at least 12 hours.

14. The method of claim 1 wherein the step of shaking and heating the frozen soaked mixture occurs for at least 12 hours.

15. The method of claim 1 wherein the step of shaking and heating the frozen soaked mixture is accomplished by means of placing the frozen soaked mixture in a container placed on the heated shaker.

16. The method of claim 1 wherein the step of evaporating includes evaporating by means of a rotary evaporator.

* * * * *